United States Patent [19]

Nelson et al.

[11] Patent Number: 4,649,275
[45] Date of Patent: Mar. 10, 1987

[54] HIGH RESOLUTION BREAST IMAGING DEVICE UTILIZING NON-IONIZING RADIATION OF NARROW SPECTRAL BANDWIDTH

[76] Inventors: Robert S. Nelson, 1045 Ocean Ave., #18, Santa Monica, Calif. 90403; Reuven D. Zach, 1425 Harper Ave., #5, Los Angeles, Calif. 90046

[21] Appl. No.: 624,467

[22] Filed: Aug. 27, 1984

[51] Int. Cl.$^4$ .................... G01N 21/27; G01N 21/59
[52] U.S. Cl. ................. 250/358.1; 250/339; 250/341; 250/360.1; 128/664; 128/665
[58] Field of Search .............. 250/341, 339, 360.1, 250/358.1; 128/664, 665

[56] References Cited

U.S. PATENT DOCUMENTS

| 4,124,301 | 11/1978 | Pocock | 356/432 |
|---|---|---|---|
| 4,203,037 | 5/1980 | Gur et al. | 378/37 |
| 4,212,306 | 7/1980 | Mahmud | 128/665 |
| 4,303,336 | 12/1981 | Cullis | 356/39 |
| 4,467,812 | 8/1984 | Stoller | 128/664 |
| 4,515,165 | 5/1985 | Carroll | 128/664 |

OTHER PUBLICATIONS

James L. Lauer and Vincent King, "Infrared Micro-Interferometer for Tissue Analysis", Proceedings of the Seventh New England Bioengineering Conference, Troy, New York (22-23 Mar. 1979), pp. 129-132.

Primary Examiner—Janice A. Howell
Assistant Examiner—Constantine Hannaher
Attorney, Agent, or Firm—Lyon & Lyon

[57] ABSTRACT

The present invention provides a method and apparatus for high resolution breast imaging which uses collimated light (in the near Ultraviolet, visible, or infra-red) of a narrow spectral bandwidth rather than ionizing X-ray radiation. The collimated light is transmitted through the breast, losing intensity due to the reflective, absorptive and refractive properties of the breast materials in the beam path. Normal and diseased breast materials may exhibit distinctive characteristics from each other when exposed to different wavelength of light. Several images can be acquired at distinct wavelengths of light to help differentiate normal and diseased breast materials. Light transmitted through the breast is recorded by a photodetector, generating an analog signal which can then be digitized and made available to a computer for analysis, processing and display. The light transmitted through the breast can be collimated to reduce the level of scattered light which reaches the photodetector, improving image quality.

31 Claims, 6 Drawing Figures

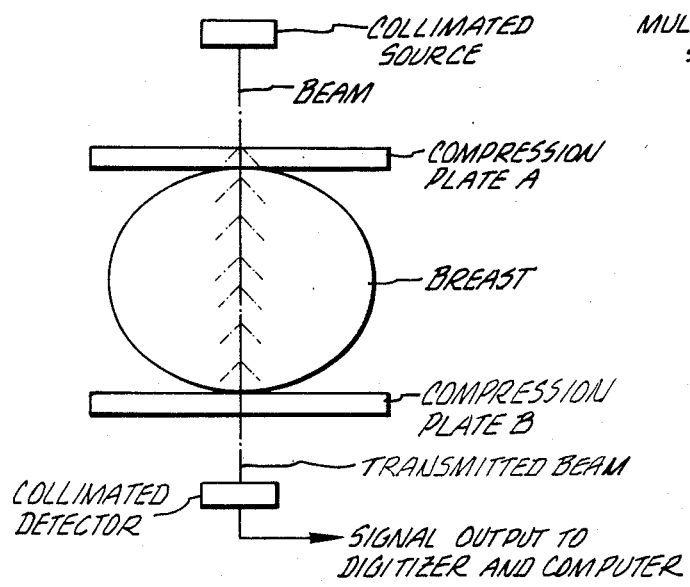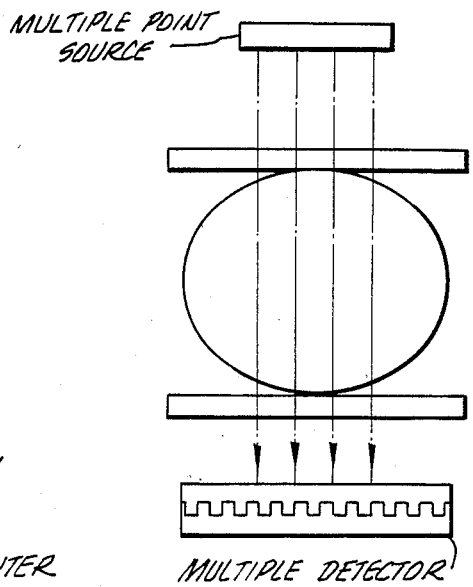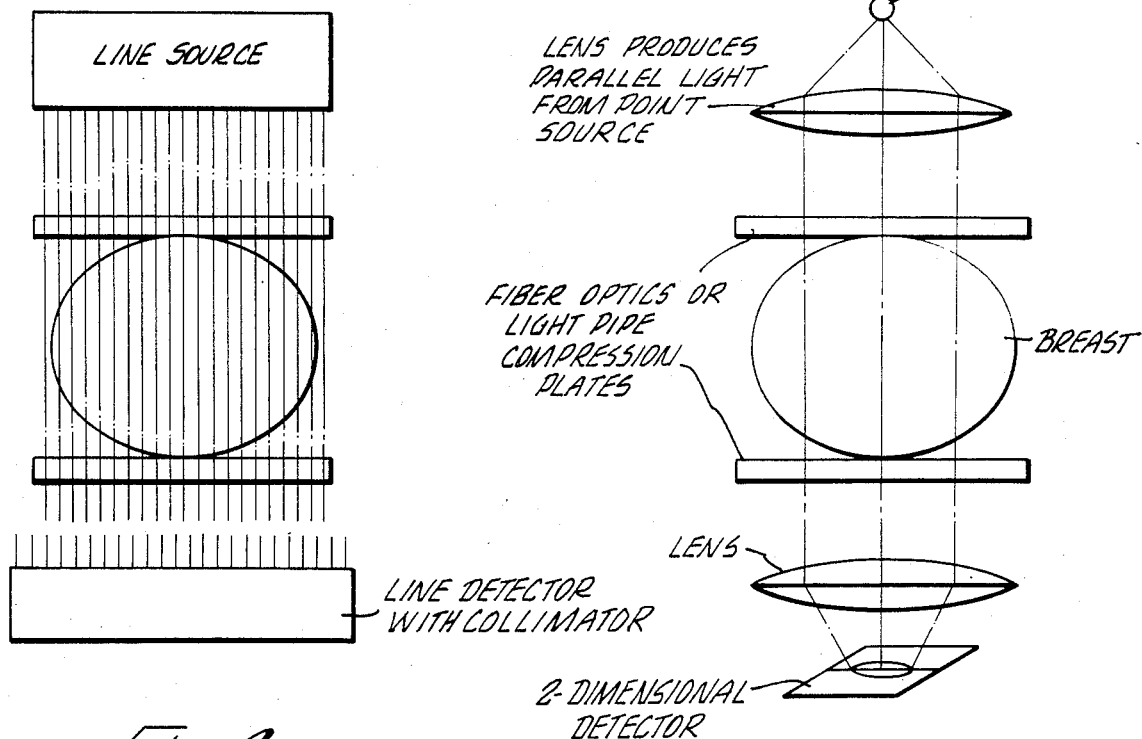

HIGH RESOLUTION BREAST IMAGING DEVICE UTILIZING NON-IONIZING RADIATION OF NARROW SPECTRAL BANDWIDTH

BACKGROUND OF INVENTION

X-ray mammography based on film-screen or Xeroradiographic detection is commonly accepted as a mass screening technique for breast disease. A certain risk is associated with this examination since X-ray radiation is also ionizing and Dedicated X-ray equipment is often required.

More recently, broad beam light sources (sometimes referred to as "light torches") with a wide spectral bandwidth in the visible and infrared have been used to examine the breast. The broad beam transmitted through the breast is usually recorded by a video camera, converted to an analog signal and viewed on a video monitor or digitized and analyzed on a computer. The ability to discriminate between various tissue-types in the breast is poor due to the wide spectral bandwidth of the transmitted beam. Resolution is lost since a large amount of scattered light is transmitted from the breast to the detector.

Lesion sizes that are detectable with this approach have generally been no smaller than what the physician can detect by palpitation. Resolution is far below that which can be obtained with X-ray imaging systems.

We realized that a collimated light source of narrow spectral bandwidth (such as generated by a Laser) could be used to produce a beam or a number of beams of very small spatial dimensions. The small spatial dimensions of the beam could be used to obtain images of the breast with high spatial resolution, whereas the narrow spectral bandwidth would improve the characterization of the composition of the breast material being imaged to be more detailed. More information could be obtained by acquiring additional images at other wavelengths of light (again, with narrow spectral bandwidths).

Although not essential to the invention disclosed, a desireable imaging format would be to have the collimated light beam(s) incident normal to the surface of the breast and to exit from the breast normal to the breast surface. The breast could be placed between two transparent plates and compressed so as to establish good surface contact and at the same time reducing the path length through the breast of the transmitted light beam(s). The compression technique is commonly employed in X-ray mammography.

The light exiting from the plate-breast-plate system could undergo additional collimation so as to reject much of the scatter component.

DESCRIPTION OF FIGURES

FIG. 2(a): A collimated pencil beam from a point source used in a raster format. The detector may use additional collimation to help minimize detection of scattered light. Collimation techniques for scatter reduction may include air gaps, fiber optics or light pipes.

FIG. 2(b): Multiple point beams used in a raster scan format to reduce image acquisition time.

FIG. 2(c): A collimated (single or multiple) line beam of light provides a line scanning format. The array of detectors would use some form of collimation to reduce detected light scatter from the subject.

FIG. 2(d): A two-dimensional, parallel light beam is used for rapid image acquisition by a two-dimensional detector. In this case the collimation is incorporated into the compression plate(s).

DESCRIPTION OF INVENTION

A method and apparatus are described for mammographic (breast imaging) applications which entail using collimated light of narrow spectral bandwidth (near Ultraviolet, Visible and Infrared) to obtain high resolution images instead of ionizing radiation (X-rays).

Resolution can be controlled by adjusting the cross-sectional area of light beam(s) before and/or after transmission through the breast. Intense, narrow spectral bandwidth sources of light appropriate for this invention include lasers or filtered light sources.

The intensity of a light beam will be reduced by absorption, reflection and refraction as it is transmitted through the breast. These optical attributes of the various normal and diseased breast materials may exhibit wavelength dependence. Thus acquiring images at different wavelengths of light may aid in distinguishing tissue types or calcifications.

The transmitted light which is recorded by a detector represent the attenuated beam plus scattered light. Collimation can be introduced before the photodetector to reduce the level of this scattered light. The photodetector produces an analog signal which can be displayed or digitized for storage and analysis on a computer.

Figure 1A:
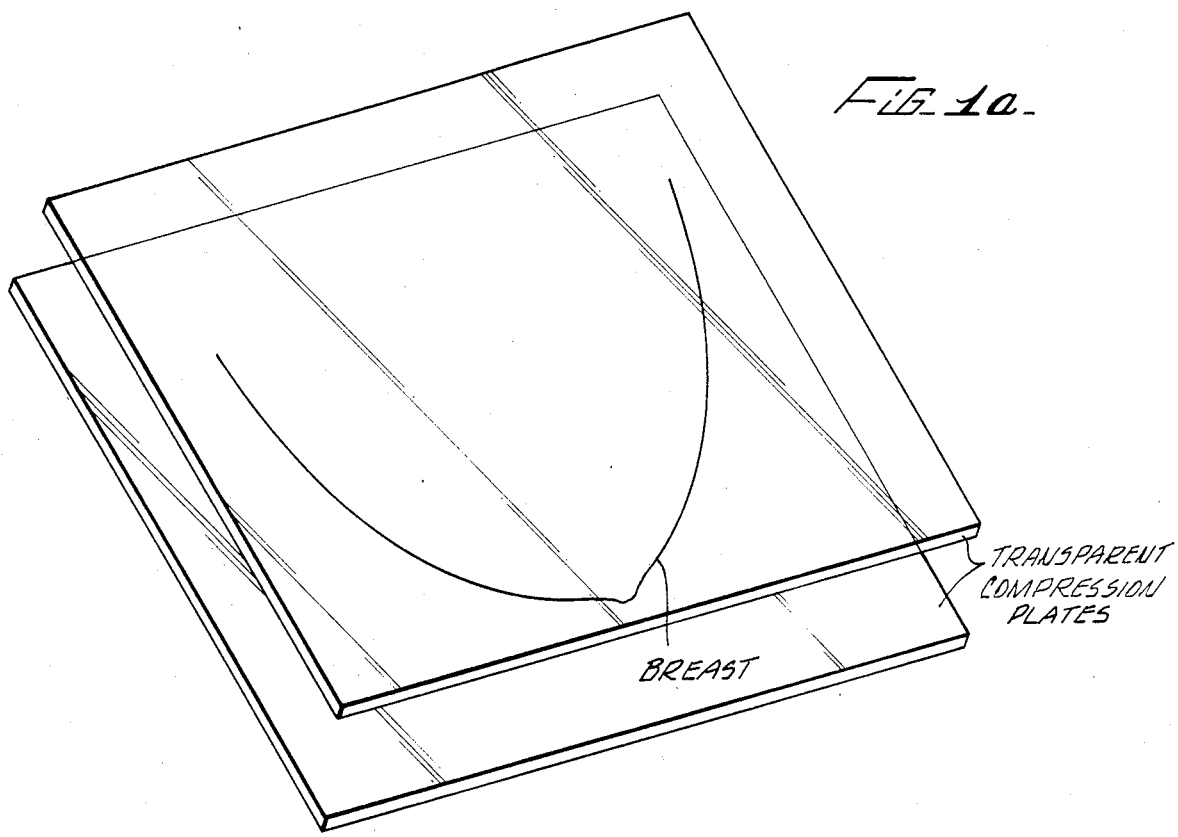
FIG. 1(a): A breast is shown in a compressed position between two transparent plates. These "compression" plates are transparent to the light wavelengths which would be used in imaging the breast. For illustrative purposes, the size of these plates is similar to those used in conventional X-ray mammography. Plate size can be reduced to permit imaging of small sections of a breast.
Figure 1B:
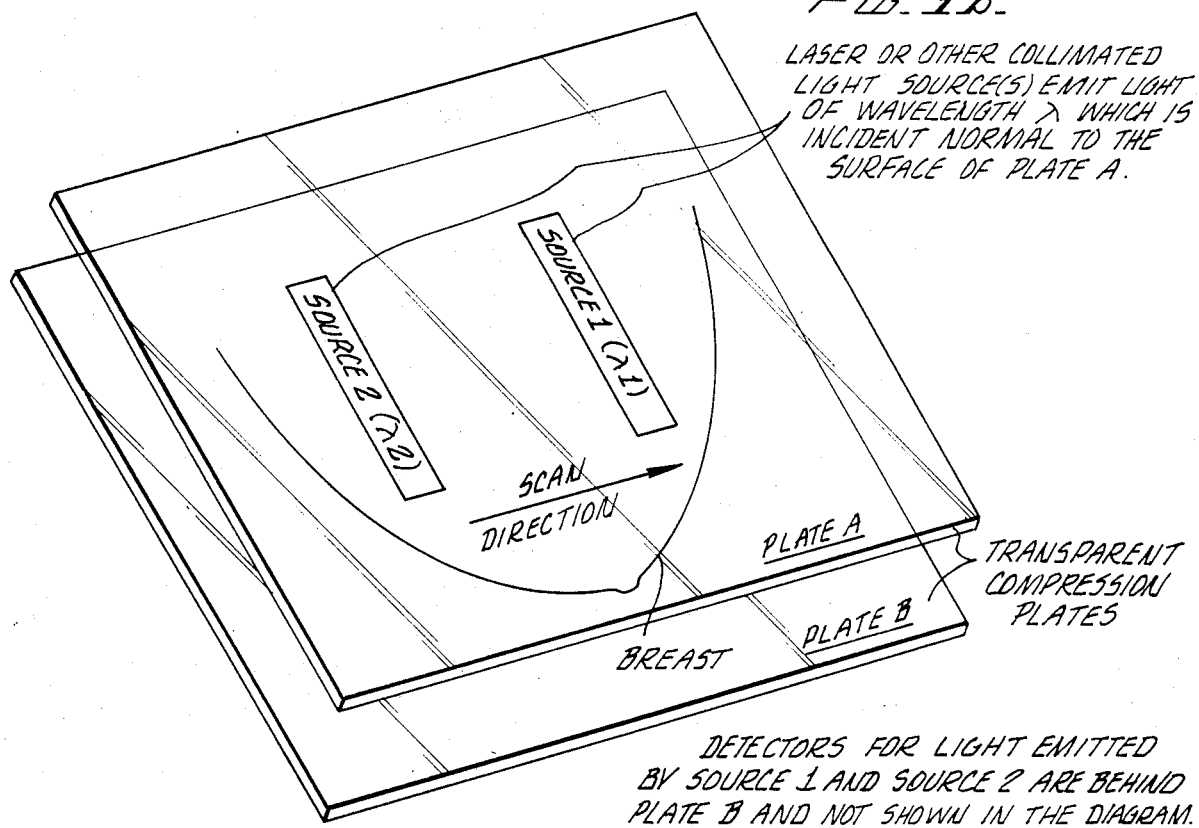
FIG. 1(b): One, two or more point, line, or two-dimensional sources, each source emitting collimated light of a distinct wavelength is (are) moved parallel to the surface of a compression plate. A detector corresponding to each source moves in synchronism with the source parallel to the surface of the second plate. Analog signals from the detector(s) can be digitized and stored in computer memory for display, processing and analysis purposes.

The breast often has an irregular shape. To reduce problems associated with light incident on and transmitted out of surfaces which are not necessarily normal to the direction of beam transmission, it is desirable to flatten the entrance and exit breast surfaces. This is easily accomplished using a pair of transparent, flat plates. As can be appreciated from FIG. 1(b), a light beam of wavelength λ1 sent from source 1 is incident normal to the surface of one compression plate. The transmitted light is attenuated by the two plates and the breast material. An image or images can be acquired by simultaneously translating one or more light source-light detector combination past the breast. Each light source emits at different wavelength (λ1≠λ2 as shown in FIG. 1(b)).

High resolution images may be obtained with a variety of scanning techniques: FIGS. 2(a,b) show a point beam or multiple point beam which could be used in a raster scan format. The transmitted light beam can be collimated by a simple air gap, fiber-optics, light-pipes or mechanical aperture to minimize detection of scattered light. This approach can be extended to include a single line or multiple line scan format as shown in FIG. 2(c).

High speed two dimensional imaging is shown in FIG. 2(d). In this case collimation (such as fiber-optics or light pipes) can be introduced into one or both compression plates.

In all cases collimation may be used to produce a beam or beams of very small cross-section and a highly directional nature. This latter attribute can be used to exclude transmitted scatter from the exit beam.

Since many versions of this invention are possible, light sources requirements may range from a continuous to a rapidly pulsed source.

It should be recognized that the foregoing are but examples of an apparatus and method within the scope of the present invention. Various modifications will occur to those with background in imaging, scanning and optics, upon reading the disclosure set forth in this document.

The invention claimed is: A device for acquiring images in mammography using light in the near UV, Visible light or Infra-red light (non-ionizing radiation).

Variations of the approach to image acquisition set forth in this document may be used for mass-screening applications in mammography and for imaging relatively transparent parts of the body, especially in very young children for whom X-ray imaging techniques are often excluded because of the high risk they pose.

What is claimed is:

1. An apparatus for obtaining mammography images using non-ionizing radiation including:
   a source of non-ionizing radiation of relatively narrow bandwidth disposed such that the radiation will be incident on a breast,
   an optical detector disposed so as to detect the radiation after having passed through the breast, and
   means for reducing the detected intensity of radiation scattered by the breast by disposing a collimator between the source of non-ionizing radiation and the optical detector.

2. The apparatus of claim 1 wherein the radiation is in the near ultraviolet, visible or infrared spectral range.

3. The apparatus of claim 1 wherein the source of non-ionizing radiation is substantially a point source, a line source or a two dimensional source.

4. The apparatus of claim 1 wherein the means for collimating the radiation is disposed between the breast and the optical detector.

5. The apparatus of claim 1 wherein the source of non-ionizing radiation has a plurality of selectable outputs of relatively narrow bandwidth.

6. An apparatus for obtaining mammography images using non-ionizing radiation including:
   one or more sources of substantially monochromatic nonionizing radiation in the near ultraviolet, visible or infrared spectral range for scanning the breast,
   a detector disposed so as to detect radiation after having passed through the breast, and
   means for reducing the detected intensity of radiation scattered by the breast by collimating the radiation after it has passed through the breast.

7. The apparatus of claim 6 wherein the source of substantially monochromatic non-ionizing radiation constitutes essentially a point source which is scanned across the breast to form an image.

8. The apparatus of claim 6 wherein the source of substantially monochromatic non-ionizing radiation constitutes essentially a line source which is scanned across the breast to form an image.

9. The apparatus of claim 6 wherein the source of substantially monochromatic non-ionizing radiation constitutes essentially continuous illumination of the breast to form an image.

10. The apparatus of claim 6 wherein the source of substantially monochromatic non-ionizing radiation provides radiation of one or more substantially monochromatic frequencies.

11. A method for obtaining mammography images using non-ionizing radiation including:
    irradiating the breast with non-ionizing radiation of a relatively narrow bandwidth,
    transmitting the radiation through the breast,
    detecting the intensity of the radiation after it has passed through the breast, and
    reducing the detected intensity of radiation scattered by the breast by collimating the radiation prior to the detection step.

12. The method for obtaining mammography images of claim 11 wherein the non-ionizing radiation is in the near ultraviolet, visible or infrared spectral range.

13. The method for obtaining mammography images of claim 11 wherein the breast is irradiated with substantially a point source or a line source or a two-dimensional source.

14. A method for obtaining mammography images using non-ionizing radiation including:
    irradiating or scanning the breast with non-ionizing radiation of a first relatively narrow bandwidth,
    transmitting the radiation through the breast,
    reducing the detected intensity of radiation scattered by the breast by collimating the radiation prior to the detection step.
    detecting the intensity of the radiation after it has passed through the breast,
    irradiating or scanning the breast with non-ionizing radiation of at least second relatively narrow bandwidth,
    transmitting, reducing the detected intensity and detecting the radiation of the second relatively narrow bandwidth as was done with the radiation of the first relatively narrow bandwidth, and
    comparing the intensity of radiation from use of the first and second relatively narrow bandwidth radiation.

15. An apparatus for obtaining mammography images using non-ionizing radiation including:
    a source of light to be placed on one side of the breast to be examined,
    a collimator which reduces the detected intensity of radiation scattered by the breast disposed between the source of light and the breast,
    a photodetector on the opposite side of the breast forming an analog signal in response to detected transmitted light,
    a computer for processing the digital signal, and
    a monitor for displaying the resultant image.

16. The apparatus claim 15 wherein the source of light is laser light.

17. The apparatus of claim 15 wherein the source of light is within the range of near ultraviolet, visible and infrared.

18. The apparatus of claim 15 where the source of light is substantially a point source.

19. The apparatus of claim 15 where the source of light is substantially a line source.

20. The apparatus of claim 15 where the source of light is a two-dimensional source.

21. The apparatus of claim 15 where a collimator is placed between the source of light and the photodetector.

22. The apparatus of claim 15 wherein the source of light is substantially monochromatic.

23. The apparatus of claim 15 wherein the source of light has a plurality of selectable monochromatic outputs.

24. The apparatus of claim 1 wherein the means for collimating the radiation constitutes a honeycomb-like structure.

25. The apparatus of claim 1 wherein the means for collimating the radiation constitutes a light-guide structure.

26. The apparatus of claim 6 wherein the means for collimating the radiation constitutes a honeycomb-like structure.

27. The apparatus of claim 6 wherein the means for collimating the radiation constitutes a light-guide structure.

28. The apparatus of claim 11 wherein the collimating is performed using a honeycomb-like structure.

29. The apparatus of claim 11 wherein the collimating is performed using a light-guide structure.

30. The apparatus of claim 15 wherein the collimator is a honeycomb-like structure.

31. The apparatus of claim 15 wherein the collimator is of a light-guide structure.

* * * * *

UNITED STATES PATENT AND TRADEMARK OFFICE
CERTIFICATE OF CORRECTION

PATENT NO. : 4,649,275

DATED : March 10, 1987

INVENTOR(S) : Robert S. Nelson & Rueven D. Zach

It is certified that error appears in the above—identified patent and that said Letters Patent is hereby corrected as shown below:

Title page:

Change "Filed: Aug. 27, 1984" to "Filed: Jun. 25, 1984."

Signed and Sealed this

Twelfth Day of June, 1990

Attest:

HARRY F. MANBECK, JR.

*Attesting Officer*  *Commissioner of Patents and Trademarks*